United States Patent
Gutkowski et al.

(10) Patent No.: US 6,596,035 B2
(45) Date of Patent: Jul. 22, 2003

(54) ONE STEP METHOD AND COMPOSITIONS FOR SIMULTANEOUSLY COLORING AND HIGHLIGHTING HAIR

(75) Inventors: Glen Alan Gutkowski, Rahway, NJ (US); Alexander Chan, Cranbury, NJ (US); Shailendra Kumar Singh, Edison, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/846,561

(22) Filed: Apr. 30, 2001

(65) Prior Publication Data

US 2001/0039685 A1 Nov. 15, 2001

Related U.S. Application Data

(63) Continuation of application No. 09/332,864, filed on Jun. 15, 1999.

(51) Int. Cl.$^7$ .................................................. A61K 7/13
(52) U.S. Cl. ........................ 8/405; 8/405; 8/110; 8/111; 8/408; 8/431; 8/534; 8/555; 8/556; 8/606; 8/649
(58) Field of Search ............................. 8/406, 408, 431, 8/534, 555, 556, 606, 649, 110, 111

(56) References Cited

U.S. PATENT DOCUMENTS 6,099,828 A * 8/2000 Kajino et al. ............ 424/70.15

FOREIGN PATENT DOCUMENTS

DE 19721785 C 1 * 9/1998 ............ A61K/7/13

* cited by examiner

Primary Examiner—Mark Kopec
Assistant Examiner—Eisa Elhilo
(74) Attorney, Agent, or Firm—Julie Blackburn

(57) ABSTRACT

A single composition for simultaneous coloring and highlighting hair to provide hair fibers having variations in tonality and hue, comprising, 1–10% inorganic persulfate, 1–20% hydrogen peroxide, 0.001–20% of at least one primary intermediate and, optionally, at least one coupler for the formation of oxidation dyes; and 0.01–20% of one or more surfactants; as well as a one step method for simultaneously color and highlighting hair to provide hair fibers having variations in tonality and hue comprising, combining, immediately prior to use, a powder composition comprised of at least one alkali metal or alkaline earth metal persulfate, an aqueous developer composition comprised of hydrogen peroxide; and an aqueous based colorant composition comprised of at least one primary intermediate and, optionally, at least one coupler for the formation of oxidation dyes; and applying the mixture to the hair for a period of time sufficient to cause coloration and highlighting of the hair.

16 Claims, No Drawings

ONE STEP METHOD AND COMPOSITIONS FOR SIMULTANEOUSLY COLORING AND HIGHLIGHTING HAIR

This application is a continuation of application Ser. No. 09/332,864 filed Jun., 15, 1999.

TECHNICAL FIELD

The invention is in the field of coloring hair, including compositions and methods for use therein.

BACKGROUND OF THE INVENTION

Hair color is used by a large percentage of the population. The reasons consumers may color hair vary from a desire to change hair color, cover grey hair, or provide unique effects such as streaking, highlighting and the like. One common complaint among haircolor users is that dyed hair often looks artificial because it does not provide the variations in tonality and hue found in natural hair. Thus, there is a need to develop methods and compositions for coloring hair that will provide more natural looking hair.

One known method for providing dyed hair with greater variability in tonality and hue is a two step procedure whereby the hair is first bleached to remove color. In the second step, hair color is applied to the bleached hair. Because the bleaching process provides uneven stripping of color from the hair, the subsequently applied color then dyes the stripped hair fibers in different shades, depending on how much color was removed by the bleaching process. This two step process is disadvantageous because it takes twice the time, and may cause increased damage to sensitive hair because both the bleach and the colorant are most often highly alkaline and are on the hair consecutively. This current method is particularly disadvantageous for those who use other hair products such as permanent waves and relaxers, which also may damage to overly sensitive hair.

U.S. Pat. No. 5,688,291 teaches a method and compositions for simultaneously lightening and coloring hair where an aqueous colorant composition containing Disperse dyes is combined with a powder bleach composition containing persulfate. The mixture is made immediately prior to use and applied to the hair. The patentee claims that hair dyed with this composition is capable of providing hightlights, or lift, to the hair. However, the Disperse dyes used in this formula are semi-permanent dyes, thus do not provide permanent color to the hair.

Japanese Patent Publication No. 08175940, published Jul. 9, 1997, teaches the combination of a xanthene-based hair dyeing agent, a peroxide based developer, and a persulfate based bleaching compound. The pH of the solution is about 7–10. However, the xanthene based dyes taught in this composition are also semi-permanent dyes and do not provide permanent color to the hair. Moreover, the xanthene based dye may be unstable in the alkaline mixture.

The object of the invention is to provide a one step method for simultaneously coloring and hightlighting hair with permanent color, to provide hair having variations in tonality and hue.

The object of the invention is to provide a one step method for coloring and hightlighting hair, particularly hair which has already been treated with coloring agents.

The object of the invention is to provide a method for coloring and highlighting hair with oxidation dyes that provide permanent color to hair.

The object of the invention is to provide a single composition for coloring and hightlighting hair without causing undue hair damage.

SUMMARY OF THE INVENTION

The invention comprises a composition for simultaneously coloring and highlighting hair to provide hair fibers having variations in tonality and hue, comprising, by weight of the total composition:
- (a) 1–10% inorganic persulfate,
- (b) 1–20% hydrogen peroxide,
- (c) 0.001–20% (combined weight) of at least one primary intermediate and, optionally, at least one coupler for the formation of oxidation dyes; and
- (d) 0.01–20% of one or more surfactants.

The invention also comprises a one step method for simultaneously coloring and highlighting hair to provide hair fibers having variations in tonality and hue comprising the steps of:
- (a) combining, immediately prior to use, (i) a powder composition comprised of at least one inorganic persulfate, (ii) an aqueous developer composition comprised of hydrogen peroxide; and (iii) an aqueous based colorant composition comprised of at least one primary intermediate and, optionally, at least one coupler for the formation of oxidation dyes; and
- (b) applying the mixture of (a) to the hair for a period of time sufficient to cause coloration and highlighting of the hair.

DETAILED DESCRIPTION

The invention comprises both a composition used to provide highlighting and coloration to hair as well as a one step method for coloring and highlighting hair. All percentages mentioned herein are percentages by weight unless otherwise indicated.

I. The Composition

The composition for simultaneously coloring and highlighting hair to provide hair fibers having variations in tonality and hue, comprises about:
- (a) 1–10% inorganic persulfate,
- (b) 1–20% hydrogen peroxide,
- (c) 0.001–20% (combined weight) of at least one primary intermediate and at least one coupler for the formation of oxidation dyes; and
- (d) 0.01–20% of one or more cationic surfactants.

The composition is prepared by mixing (i) a powder bleach composition, (ii) an aqueous developer composition; and (iii) an aqueous based colorant composition comprised of at least one primary intermediate and, optionally, at least one coupler for the formation of oxidation dyes prior to application to the hair.

A. The Powder Bleach Composition

The powder bleach composition is generally a mixture of persulfate compounds which are capable of bleaching the hair, particulate fillers, and, if desired, inorganic particulate colorants.

1. Persulfates

The powder bleach composition comprises 15–65%, preferably 20–60%, more preferably 25–55% by weight of the total composition of at least one inorganic persulfate which may be ammonium persulfate, or an alkali metal or alkaline earth metal persulfate. Preferred are alkali metal or alkaline earth metal persulfates. Examples of alkali metal persulfates include lithium, sodium, potassium, cesium, and the like. Examples of suitable alkaline earth metals include magnesium, calcium, and the like. Particularly preferred are sodium and potassium persulfates. The persulfates are generally in particulate form, and have particle sizes ranging from about 0.1 to 200 microns.

2. Particulate Fillers

The remainder of the powder bleach composition comprises particulate fillers. Preferably, the powder bleach composition comprises 5–60%, preferably 8–55%, more preferably 10–50% by weight of the total composition of the particulate fillers. The term "particulate filler" means a generally inert particulate having a particle size of about 0.1–250 microns. The particulate fillers provide volume and, when mixed with the persulfates, dilute the persulfate particles. A variety of particulate fillers are suitable including inorganics, inorganic salts, hydrophilic colloids, carbohydrates, soaps, alkyl sulfates, and the like.

(a) Inorganics

Examples of inorganics include silica, hydrated silica, alumina, attapulgite, bentonite, calcium oxide, chalk, diamond powder, diatomaceous earth, fuller's earth, hectorite, kaolin, mica, magnesium oxide, montmorillonite, pumice, talc, tin oxide, zeolite, zinc oxide, and the like.

(b) Inorganic Salts

Examples of suitable inorganic salts include aluminum, sodium, potassium, and magnesium salts of inorganic or organic acids. Examples of suitable salts include sodium metasilicate, sodium chloride, sodium silicate, aluminum citrate, calcium saccharin, calcium salicylate, calcium citrate, calcium benzoate, magnesium acetate, magnesium ascorbate, magnesium PCA, magnesium gluconate, potassium acetate, potassium benzoate, potassium citrate, potassium sorbate, sodium acetate, sodium ascorbate, sodium citrate, sodium gluconate, sodium pyruvate, and mixtures thereof.

(c) Hydrophilic Colloids

Examples of suitable hydrophilic colloids include hydroxyethylcellulose, locust bean, maltodextrin, methylcellulose, agar, dextran, dextran sulfate, gelatin, pectin, potassium alginate, sodium carboxymethylchitin, xanthan gum, and the like.

(d) Carbohydrates

Examples of suitable carbohydrates include sugars such as glucose, sucrose, maltose, xylose, trehelose, and derivatives thereof, in particular sugar esters of long chain, $C_{14-30}$ fatty acids, as well as dextrins, cellulosics, and derivatives thereof.

(e) Soaps and Alkyl Sulfates

Examples of soaps and alkyl sulfate particles that may act as particulate fillers include the aluminum, sodium, and potassium salts of fatty acids such as aluminum distearate, aluminum isostearate, aluminum myristate, calcium behenate, calcium stearate, calcium behenate, magnesium stearate, magnesium tallowate, potassium palmitate, potassium stearate, potassium oleate, sodium stearate, sodium oleate, sodium myristate, sodium palmitate, and the like. Suitable alkyl sulfates include sodium lauryl sulfate, sodium cetyl sulfate, sodium myristyl sulfate, sodium octyl sulfate, and the like.

3. Inorganic Colorants

If desired, the powder bleach composition may comprise 0.01–2%, preferably 0.05–1%, more preferably about 0.1–1% of an inorganic colorant. The inorganic colorant is preferably in the particulate form and will provide a subtle coloration to the powder composition to make it more aesthetically pleasing for commercial purposes. Particularly preferred for use in the bleach composition is ultramarine blue.

B. The Aqueous Developer Composition

The aqueous developer composition comprises, by weight of the total composition, 50–99% water, 1–30% hydrogen peroxide, and 0.01–30%, preferably 0.05–20%, more preferably 0.1–15% of an oily phase. The aqueous developer composition may be in the form of a water-in-oil or oil-in-water emulsion.

1. Oily Phase Ingredients

Suitable oils are liquid at room temperature (25° C.) and include hydrocarbon oils and/or silicone oils which are volatile or nonvolatile, and glyceryl esters of fatty acids. The term "volatile" means that the oil has a measureable vapor pressure, i.e. a vapor pressure of at least 2 mm. of mercury at 20° C. The term "nonvolatile" means that the oil has a vapor pressure of less than 2 mm. of mercury at 20° C. Suitable volatile oils generally have a viscosity of 0.5 to 10 centistokes at 25° C., and include linear silicones, cyclic silicones, paraffinic hydrocarbons, or mixtures thereof.

(a) Volatile Silicones

Cyclic silicones (or cyclomethicones) are of the general formula:

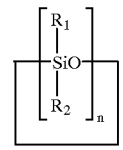

wherein $R_1$ and $R_2$ are each independently H, $C_{1-8}$ alkyl, aryl, aralkyl, alkenyl, or a cyclic or alicyclic ring, preferably a $C_{1-4}$ alkyl, most preferably methyl, and wherein n=3–7.

Linear volatile silicones in accordance with the invention have the general formula.

where n=0–6, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

(b) Volatile Paraffinic Hydrocarbons

Also suitable as the volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable. Transfer resistant cosmetic sticks of the invention will generally comprise a mixture of volatile silicones and volatile paraffinic hydrocarbons.

(c) Nonvolatile Silicones

Nonvolatile silicones, both water soluble and water insoluble, are also suitable as the oil component. Such silicones preferably have a viscosity of 10 to 600,000 centistokes, preferably 20 to 100,000 centistokes at 25° C. Suitable water insoluble silicones include amodimethicone, bisphenylhexamethicone, dimethicone, hexadecyl methicone, methicone, phenyl trimethicone, simethicone, dimethylhydrogensiloxane, stearoxytrimethylsilane, vinyldimethicone, and mixtures thereof. Also suitable are water soluble silicones such as dimethicone copolyol, dimethiconol, and the like. Such silicones are available from Dow Corning as the 3225C formulation aid, Dow 190 and 193 fluids, or similar products marketed by Goldschmidt under the ABIL tradename.

(d) Esters

Other nonvolatile oils include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl.

(e) Glyceryl Esters of Fatty Acids

Also suitable are naturally occuring glyceryl esters of fatty acids, or triglycerides as well as synthetic or semi-synthetic glyceryl esters.

(f) Nonvolatile Hydrocarbons

Also suitable for use are nonvolatile hydrocarbons such as isoparaffins, hydrogenated polyisobutene, mineral oil, squalene, and so on.

(g) Vegetable Oils

Also suitable for use are one or more vegetable oils obtained from plants such as flowers or vegetables. Examples of such oils include meadowfoam seed oil, borage oil, cottonseed oil, linseed oil, peanut oil, and so on.

2. Nonionic Surfactants

If desired, the aqueous developer composition may contain one or more nonionic surfactants. Recommended ranges are 0.01–10%, preferably 0.05–8%, more preferably 0.1–7% by weight of the total composition.

(a) Alkoxylated Alcohols

Suitable nonionic surfactants include alkoxylated alcohols, or ethers, formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on. Particularly preferred is Ceteareth 20, which is the reaction product of a mixture of cetyl and stearyl alcohol and ethylene oxide, wherein the number of repeating ethylene oxide units in the molecule is 20. Also preferred are C12–16 pareth-9, which is the reaction product of C12–16 fatty alcohols and ethylene oxide wherein the number of repeating ethylene oxide units in the molecule is nine; and trideceth-12, which is the reaction product of tridecyl alcohol and ethylene oxide wherein the average number of repeating ethylene oxide units in the molecule is 12.

(b) Alkoxylated Carboxylic Acids

Also suitable as the nonionic surfactant are alkyoxylated carboxylic acids, which are formed by the reaction of a carboxylic acid with an alkylene oxide or with a polymeric ether. The resulting products have the general formula:

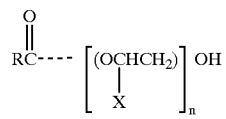

or

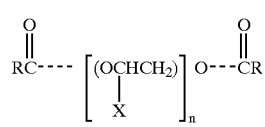

where RCO is the carboxylic ester radical, X is hydrogen or lower alkyl, and n is the number of polymerized alkoxy groups. In the case of the diesters, the two RCO-groups do not need to be identical. Preferably, R is a $C_{6-30}$ straight or branched chain, saturated or unsaturated alkyl, and n is from 1–100.

(c) Sorbitan Derivatives

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

d) Alkyl Polysaccharides

Also suitable are alkyl polysaccharides having a hydrophobic group of 6 to 30, preferably 10, carbon atoms and a polysaccharide group such as glucose, galactose, etc. Suitable alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and so on.

3. Thickening Agents

The aqueous developer composition may also comprise a thickening agent, if desired. Preferably, the amount of thickening agent is 0.001–5%, preferably 0.005–4%, more preferably 0.005–3% by weight of the total composition.

(a) Acrylic Copolymer Thickeners

One type of thickening agent for use in the developer composition is an acrylic polymer comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alkyl methacrylate, and mixtures thereof. Preferably, the A monomer comprises one or more of acrylic acid or methacrylic acid, and the B monomer comprises is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. Most preferably, the acrylic copolymer is supplied in an aqueous solution having a solid content ranging from about 10–60%, preferably 20–50%, more preferably 25–45% by weight of the polymer, with the remainder water. Preferably, the thickening agent is a poly mer comprised of A, B, and C monomers wherein A and B are as defined above, and C has the general formula:

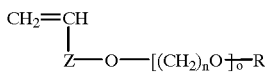

Preferably, in the copolymer used for the secondary thickening agent in the preferred embodiment of the invention, A and B are as above defined; and in the C monomer Z is $(CH_2)_m$, m is 1–2, n is 2, and o is 2–100, and R is a $C_{12-22}$ straight or branched chain alkyl. More preferably in the C monomer m is 1, n is 2, o is 10, and R is $C_{18}$ or stearyl, and the compound is steareth-10 allyl ether/acrylate copolymer, which may be purchased from Allied Colloids under the tradename Salcare SC90.

C. The Aqueous Based Hair Colorant

The aqueous based hair colorant composition contains at least one primary intermediate and, optionally, at least one coupler for the formation of oxidation dyes in aqueous medium. Preferably, the aqueous based colorant composition has a pH of about 7 to 11, and may be in the form of a water-in-oil or oil-in-water emulsion. The colorant composition may additionally comprise one or more of a quaternary ammonium surfactant, protein derivative, silicone oil, and a nonionic, zwitterionic, or betaine surfactant.

1. Primary Intermediates and Couplers

The aqueous based hair colorant composition comprises about 0.001–20%, 0.005–8%, more preferably 0.01–7% (combined weight) of one or more primary intermediates and, optionally, couplers for oxidation dyes. Preferably, the range of primary intermediate will be about 0.0001–5% by weight and the range of coupler will be about 0.0001–5% by weight. Primary intermediates and couplers are well known hair coloring ingredients, and include ortho, meta, or para substituted aminophenols or phenylenediamines, such as para-phenylenediamines of the formula:

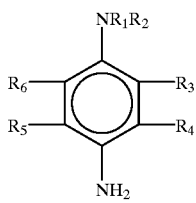

wherein $R_1$ and $R_2$ are each independently hydrogen, $C_{1-6}$ alkyl, or $C_{1-6}$ alkyl substituted with one or more hydroxy, methoxy, methylsulphonylamino, aminocarbonyl, furfuryl, unsubstituted phenyl, or amino substituted phenyl groups; $R_3$ and $R_6$ are each independently hydrogen, $C_{1-6}$ alkyl, $C_{1-6}$ alkoxy, halogen, or $C_{1-6}$ alkyl substituted with one or more hydroxyl groups; and $R_4$ and $R_5$ are each independently hydrogen, $C_{1-6}$ lower alkoxy, $C_{1-6}$ lower alkyl, or halogen. Examples of suitable primary intermediates are para-aminophenol, resorcinol, ortho-aminophenols, ortho-phenylenediamines, and heterocyclic compounds. Examples of suitable primary intermediates include para-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropyl-4-aminobenzene, 2,6-dimethyl-3-methoxy-1,4-diaminobenzene, 1-amino-4-hydroxybenzene, and derivatives thereof.

Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

Suitable couplers include, for example, those having the general formula:

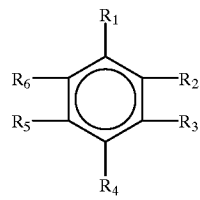

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ alkoxy, $C_{1-6}$ hydroxyalky, or $C_{1-6}$ alkyl, or $R_3$ and $R_4$ together may form a methylenedioxy or ethylenedioxy group. Examples of such compounds include meta-derivatives such as phenols, meta-aminophenols, meta-phenylenediamines, and the like, which may be unsubstituted, or substituted on the amino group or benzene ring with alkyl, hydroxyalkyl, alkylamino groups, and the like. Suitable couplers include 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethyloxy-1,3-diaminobenzene, 6-methoxy-5-ethyl-1,3-diaminobenzene, 6-ethyloxy-1,3-diaminobenzene, 1-bis(beta-hydroxyethyl)amino-3-aminobenzene, 2-methyl-1,3-diaminobenzene, 6-methoxy-1-amino-[(beta-hydroxyethyl)amino]-benzene, 6-(beta-aminoethyloxy)-1,3-diaminobenzene, 6-(beta-hydroxyethyloxy)-1-amino-3-(methylamino)benzene, 6-carboxymethyloxy-1,3-diaminobenzene, 6-ethyloxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino) benzene, 6-hydroxybenzomorpholine, 4-methyl-6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, and mixtures thereof.

Preferred couplers include resorcinol, 1-naphthol, 5-amino-o-cresol, 2-methylresorcinol, m-aminophenol, m-phenylenediamine, 1-phenyl-3-methyl-pyrazol-5-one, their salts, or mixtures thereof.

2. Cationic Surfactants

Preferably the aqueous based colorant composition comprises 0.001–10%, more preferably 0.005–8%, most preferably 0.01–5% of a cationic surfactant. Suitable cationic surfactants include cationic polymers, quaternary ammonium salts or the salts of fatty amines.

(a) Quaternary Ammonium Compounds

Quaternary ammonium compounds, or salts, have the formula:

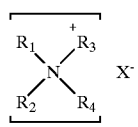

wherein $R_1$, $R_2$, $R_3$, and $R_4$ are each independently an aliphatic group of 1 to 22 carbon atoms, or aromatic, alkyl, hydroxyalkyl, aryl, or alkaryl group having 12 to 22 carbon atoms; with the proviso that there is at least one alkyl group having 12 to 22 carbon atoms. Preferably at least one of $R_1$, $R_2$, $R_3$, and $R_4$ are methyl while the remaining substituents are $C_{12-22}$ aliphatic radicals. X is an anion selected from halogen, acetate, phosphate, nitrate and methyl sulfate, tosylate, and hydroxide radicals. The aliphatic groups may contain, in addition to carbon atoms, ether linkages as well as amido groups. Suitable quaternary ammonium compounds may be mono-long chain alkyl, di-long chain alkyl, tri-long chain alkyl, and the like. Examples of such quaternary ammonium salts include behenalkonium chloride, behentrimonium chloride, behentrimonium methosulfate, benzalkonium chloride, benzethonium chloride, benzyl triethyl ammonium chloride, cetalkonium chloride, cetrimonium chloride, cetrimonium bromide, cetrimonium methosulfate, cetrimonium tosylate, cetylpyridinium chloride, dibehenyl/diarachidyl dimonium chloride, dibehenyldimonium chloride, dibehenyldimonium methosulfate, dicapryl/dicaprylyl dimonium chloride, and the like.

Other quaternary ammonium salts useful as the cationic surfactant include compounds of the general formula:

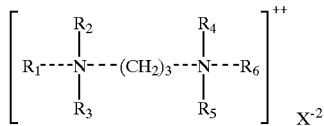

wherein at least one of $R_{1-6}$ is an aliphatic group having 16 to 22 carbon atoms, and the remaining $R_{1-6}$ are the same or different and are selected from alkyls having 1 to 4 carbon atoms and X is an anion as above defined.

(b) Amides

Amides which exhibit the general formulas set forth below are also suitable cationic surfactants:

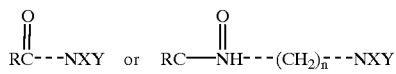

wherein R is a straight or branched chain saturated or unsaturated alkyl having 6 to 30 carbon atoms, n is an integer from 1 to 4, and X and Y are each independently H, or $C_{1-6}$ alkyl.

Preferred is an amide of the formula:

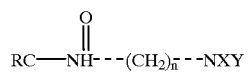

wherein R is a $C_{12-22}$ straight or branched chain alkyl, n is an integer from 1 to 4, and X is lower alkyl, preferably methyl.

(c) Amidoamine Salts

Also suitable are amidoamine salts, which are the condensation products of fatty acids with a polyfunctional amines, for example, those having the formula $RCONH(CH_2)_nNR_1R_2$ where RCO is a fatty acyl group such as stearoyl, $R_1$ and $R_2$ are methyl or ethyl, and n is 2 or 3. Examples of such compounds include stearamidopropyl dimethylamine. Particularly preferred are amidoamine compounds complexed with a mild dimer acid, such as di(behenamidopropyl dimethyl amine) dimer dilinoleate or di(linoleamidopropyl dimethyl amine) dimer linoleate. Both ingredients are sold by Alzo, Inc. under the NECON tradename.

(d) Quaternary Imidazolinium Salts

Also, quaternary imidazolinium salts having the following general formula are suitable as the cationic surfactant:

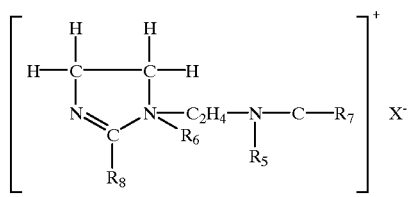

wherein $R_5$ is hydrogen or a $C_{1-4}$ alkyl; $R_6$ is a $C_{1-4}$ alkyl; $R_7$ is a $C_{8-22}$ alkyl; and $R_8$ is hydrogen, or a $C_{1-22}$ alkyl; and X is an anion as defined above.

(e) Amine Salts

Also suitable as the cationic surfactant are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine, ethyl stearamine, and so on.

(f) Cationic Polymers

Also suitable as the cationic surfactant are cationic polymers such as:

(i) Quaternary Derivatives of Cellulose Ethers

Examples of quaternary derivatives of cellulose ethers are polymers sold under the tradename JR-125, JR-400, JR-30M, which have the CTFA name Polyquaternium-10. These polymers are quaternary ammonium salts of hydroxyethylcellulose which is reacted with trimethyl ammonium substituted epoxide.

(ii) Copolymers of Vinylpyrrolidone

Copolymers of vinylpyrrolidone having monomer units of the formula:

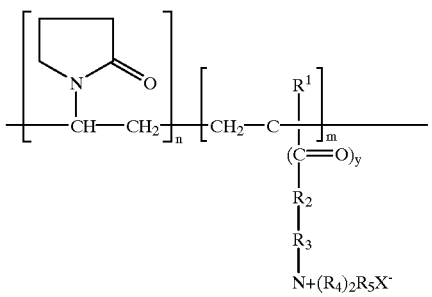

wherein $R^1$ is hydrogen or methyl, preferably methyl;

y is 0 or 1, preferably 1

$R^2$ is O or NH, preferably NH;

$R^3$ is $C_xH_{2x}$ where x is 2 to 18, or —$CH_2$—CHOH—$CH_2$, preferably $C_xH_{2x}$ where x is 2;

$R^4$ is methyl, ethyl, phenyl, or $C_{1-4}$ substituted phenyl, preferably methyl; and $R^5$ is methyl or ethyl, preferably methyl.

Preferably the copolymer is a polymeric quaternary ammonium salt consisting of vinyl pyrrolidone and dimethyl aminopropyl methacrylamide monomers which has the CTFA name Polyquaternium-28.

(iii) Polymers of Dimethyldiallylammonium Chloride

Homopolymers of dimethyldiallylammonium chloride, or copolymers of dimethyldiallylammonium chloride and acrylamide are also suitable. Such compounds are sold under the tradename MERQUAT by Merck.

(iv) Acrylic or Methacrylic Acid Polymers

Homopolymers or copolymers derived from acrylic or methacrylic acid, selected from monomer units acrylamide, methylacrylamide, diacetone-acrylamide, acrylamide or methacrylamide substituted on the nitrogen by lower alkyl, alkyl esters of acrylic acid and methacrylic acid, vinylpyrrolidone, or vinyl esters are suitable for use.

(v) Cationic Silicones

As used herein, the term "cationic silicone" means any silicone polymer or oligomer having a silicon backbone, including polysiloxanes, having a positive charge on the silicone structure itself. Cationic silicones that may be used in the compositions of the invention include those corresponding to the following formula, where the ratio of D to T units, if present, are greater than about 80 D units to 1 T unit:

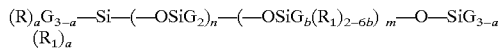

in which G is selected from the group consisting of H, phenyl, OH, $C_{1-10}$ alkyl, and is preferably $CH_3$; and a is 0 or an integer from 1 to 3, and is preferably 0; b is 0 or 1, preferably 1; the sum n+m is a number from 1 to 2,000 and is preferably 50 to 150; n is a number from 0 to 2000, and is preferably 50 to 150; and m is an integer from 1 to 2000, and is preferably 1 to 10; R is a $C_{1-10}$ alkyl, and $R_1$ is a monovalent radical of the formula $C_qH_{2q}L$ in which q is an integer from 2 to 8 and L is selected from the groups:

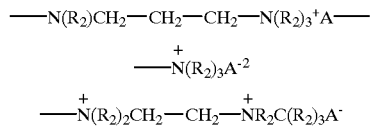

in which $R_2$ is selected from the group consisting of H, phenyl, benzyl, a saturated hydrocarbon radical, and is preferably an alkyl radical containing 1–20 carbon atoms; and A— is a halide, methylsulfate, or tosylate ion.

(vi) Polymeric Quaternary Ammonium Salts

Also suitable are polymeric quaternary ammonium salts such as Polyquaternium 31, 33, 34, 35, 36, 37, and 39.

(vii) Diquaternary Polydimethylsiloxanes

Also suitable are diquaternary polydimethylsiloxanes such as Quaternium-80, sold by Goldschmidt Corporation under the tradename ABIL-Quat 3272.

Examples of other cationic polymers that can be used in the compositions of the invention are disclosed in U.S. Pat. Nos. 5,240,450 and 5,573,709, which are hereby incorporated by reference.

The preferred aqueous based colorant compositions of the invention contain 0.001–10% by weight of a cationic surfactant which comprises one or more cationic polymers, in particular, derivatives of cellulose ether either alone or in combination with a copolymer of vinyl pyrrolidone. Most preferred is a composition comprising a mixture of Polyquaternium-10 and Polyquaternium-28.

3. Oily Ingredients

The aqueous based colorant composition may additionally comprise one or more oils, as described above with respect to the aqueous developer composition. Preferably the aqueous based colorant composition comprises 0.001–20%, more preferably 0.005–15%, most preferably 0.01–10% by weight of the total composition of one or more oils. The colorant may be in the form of a water-in-oil or oil-in-water emulsion form. Preferably the oils are either volatile or nonvolatile silicones as discussed herein with respect to the aqueous developer. Particularly preferred are silicones such as dimethicone copolyol, dimethicone, and cyclomethicone.

4. Humectants

It may be desireable to incorporate one or more humectants into the aqueous colorant composition. Preferably the colorant composition comprises 0.01–10%, more preferably 0.05–8%, most preferably 0.1–5% by weight of the total composition of humectant. Suitable humectants include monomeric, homopolymeric, and/or block copolymeric ethers as well as mono-, di-, or polyhydric alcohols.

Suitable ethers are formed by the polymerization of monomeric alkylene oxides, generally ethylene or propylene oxide. Such polymeric ethers have the following general formula:

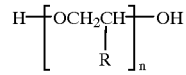

wherein R is H or lower alkyl and n is the number of repeating monomer units, and ranges from 1 to 500.

Also suitable are polyols such as glycerine or $C_{1-4}$ alkylene glycols and the like. Particularly preferred are $C_{1-4}$ alkylene glycols, in particular propylene and/or butylene glycol and ethoxydiglycol.

5. Anionic Zwitterionic Betaine, or Noninic Surfactants

If desired, the aqueous colorant composition may comprise one or more of an anionic, zwitterionic, betaine, or nonionic surfactant, in the range of about 0.01–15%, preferably 0.05–10%, more preferably 0.1–8% by weight of the total composition.

(a) Anionic Surfactants

Suitable anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide. The fatty acids may be derived from coconut oil, for example.

In addition, succinates and succinimates are suitable anionic surfactants. This class includes compounds such as disodium N-octadecylsulfosuccinate; tetrasodium N-(1,2-dicarboxyethyl)-N-octadecylsufosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sulfones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

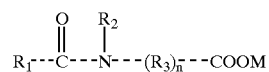

wherein $R_1$ is a $C_{8-24}$ alkyl or alkenyl radical, preferably $C_{10-18}$; $R_2$ is H, $C_{1-4}$ alkyl, phenyl, or—$CH_2COOM$; $R_3$ is $CX_2$— or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms. Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

(b) Amphoteric Surfactants

Suitable amphoteric surfactants may be imidazolinium compounds having the general formula:

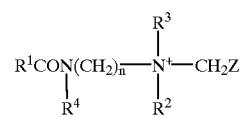

wherein $R^1$ is $C_{8-22}$ alkyl or alkenyl, preferably $C_{12-16}$; $R^2$ is hydrogen or $CH_2CO_2M$, $R^3$ is $CH_2CH_2OH$ or $CH_2CH_2OCH_2CHCOOM$; $R^4$ is hydrogen, $CH_2CH_2OH$, or $CH_2CH_2OCH_2CH_2COOM$, Z is $CO_2M$ or $CH_2CO_2M$, n is 2 or 3, preferably 2 M is hydrogen or a cation such as an alkali metal, alkaline earth metal, ammonium, or alkanol ammonium cation. Examples of such materials are marketed under the tradename MIRANOL, by Miranol, Inc.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants include aminoalkanoates of the formula

or iminodialkanoates of the formula:

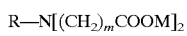

and mixtures thereof; wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-iminodipropionic acid, or mixtures thereof.

(c) Zwitterionic Surfactants

Zwitterionic surfactants are also suitable for use in the compositions of the invention. The general formula for such surfactants is:

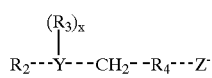

wherein $R_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or monohydroxyalkyl group containing about 1 to 3 carbon atoms; X is 1 when Y is a sulfur atom, and 2 when Y is a nitrogen or phosphorus atom; $R_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionics include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof Also suitable are sulfo- and amido-betaines such as coco dimethyl sulfopropyl betaine, cocamidopropyl betaine, stearyl dimethyl sulfopropyl betaine, and the like. Particularly preferred for use in the aqueous colorant composition is a betaine surfactant, in particular, cocamidopropyl betaine.

(d) Nonionic Surfactants

Suitable nonionic surfactants are those mentioned above with respect to the developer composition, and in the same percentage ranges.

6. Protein Derivatives

It may be desired to incorporate one or more protein derivatives into the colorant composition to provide hair conditioning and moisturizing benefits in a range of about 0.01–15%, preferably 0.05–10%, more preferably 0.1–8% by weight of the total composition. The protein derivatives are generally formed by subjecting animal or vegetable proteins to enzymatic or chemical hydrolysis. If desired, the hydrolysate may be further reacted with other compounds to provide further derivatives. Examples of protein derivatives which are suitable for use in the compositions include hydrolysates of collagen, casein, albumen, egg protein, elastin, keratin, silk, soy protein, vegetable protein, wheat protein, wheat starch, wheat gluten, pea protein, oat protein, placental protein, and so on. Also suitable are derivatives of such hydrolysates, such as the reaction product of the hydrolysate with various fatty acids. Examples of such reaction products include potassium cocoyl hydrolyzed casein, collagen, corn protein, keratin, potato protein, rice bran protein, silk, marine collagen, and so on. Particularly preferred are hydrolysates of wheat protein.

II. The Method

Immediately prior to use, the powder bleach composition, the aqueous developer, and the aqueous colorant composition are mixed to form the following composition:

(a) 1–10% alkali metal or alkaline earth metal persulfate,
(b) 1–20% hydrogen peroxide,
(c) 0.01–10% of one or more primary intermediates and couplers for oxidation dyes; and
(d) 0.01–20% of one or more cationic surfactants.

Preferably, the above composition is obtained by combining about 1–20% of the bleach powder, about 50–90% of the aqueous developer, and about 10–60% of the aqueous colorant composition, all percentages being by weight of the total mixture. More preferably, the mixture is made by combining about 4.2% bleach powder, 72% aqueous developer, and 23.8% aqueous colorant composition.

The mixture is prepared immediately prior to use and applied to the hair. The mixture may be applied to the entire head of hair. It may also be desired to apply the mixture only to select strands of hair. In this case, a streaking cap or something similar is applied to the hair and as strands of hair are pulled through the holes in the cap. The mixture is applied to the hair and allowed to remain for about 5–35, preferably 10–25 minutes, or until the color has had an adequate amount of time to lighten the original color and to deposit new color on the hair. The hair is then rinsed well with water to remove the colorant. The hair is then either directly conditioned with a hair conditioner, or if desired, the hair is first shampooed and then treated with a conditioner. The colored hair has variations in tonality and hue which make it look very natural. In addition, the hair is soft and healthy, and does not exhibit the dry, damaged feel and appearance that often characterizes hair colored with oxidation dyes.

The invention will be further described in connection with the following examples, which are set forth for the purposes of illustration of only.

EXAMPLE 1

A powder composition, aqueous developer composition, and aqueous based colorant composition were prepared as follows:

| Powder Bleach Composition | |
|---|---|
| | w/w % |
| Potassium persulfate | 45.00 |
| Sodium persulfate | 5.00 |
| Sodium metasilicate | 11.50 |
| Silica | 2.00 |
| Hydrated silica | 2.00 |
| Sodium stearate | 10.67 |
| EDTA | 2.00 |
| Hydroxyethylcellulose | 3.09 |
| Sodium lauryl sulfate | 2.00 |
| Sodium chloride | 5.00 |
| Sucrose | 7.16 |
| Ultramarine blue | 0.08 |
| Sodium silicate | 4.50 |

The bleach composition was made by combining all of the ingredients and mixing well.

| Peroxide Developer | |
|---|---|
| | w/w % |
| Water | QS |
| Methyl paraben | 0.05 |
| EDTA | 0.02 |
| Mineral oil | 0.60 |
| Cetearyl alcohol/ceteareth-20 (80:20) | 3.60 |
| Lauryl pyrrolidone | 2.00 |
| Cyclomethicone/trimethylsiloxysilicate (50:50) | 0.01 |
| Trimethylsilylamodimethicone/C11–15 pareth-7/ | 1.75 |

-continued

Peroxide Developer

| | w/w % |
|---|---|
| C12–16 pareth-9/trideceth-12/glycerin/water (20:6:4:2:3:65) | |
| Disodium phosphate | 0.022 |
| Phosphoric acid | 0.015 |
| Hydrogen peroxide (35% aqueous solution) | 26.00 |
| Steareth-10 allyl ether/acrylates copolymer | 2.00 |

The composition was made by combining all of the ingredients and mixing well.

Colorant Composition

| | w/w % |
|---|---|
| Water | QS |
| Propylene glycol | 4.00 |
| Ethoxydiglycol | 2.00 |
| Tetrasodium EDTA (38% aqueous solution) | 0.80 |
| Ethanolamine | 5.00 |
| Hypnea Musciformis Extract, Gellidiela Acerosa extract Sargassum Filipendula extract, sorbitol. | 0.80 |
| Sodium tinuvin sulfonate, buteth-3, propane tricarboxylic acid | 1.00 |
| Erythorbic acid | 0.20 |
| Sodium sulfite | 0.50 |
| Primary intermediates and couplers | 0.3145 |
| Ammonium lauryl sulfate (28% aqueous solution) | 2.00 |
| Oleic acid | 12.50 |
| Cetearyl alcohol | 4.00 |
| Emulsifying wax | 2.00 |
| Oleth-20 | 1.00 |
| Steareth-21 | 0.700 |
| Meadowfoam seed oil | 0.750 |
| Oleyl alcohol | 0.400 |
| Polyquaternium-10 | 0.200 |
| Polyquaternium-28 | 0.500 |
| Mica/titanium dioxide | 0.300 |
| Hydrolyzed wheat protein | 1.00 |
| Wheat amino acids | 1.00 |
| Fragrance | 0.75 |
| Ammonium hydroxide (27.5% aqueous solution) | 7.00 |

The colorant composition was made by combining all ingredients and mixing well. The pH of the composition was about 8.

The bleach composition, developer composition, and colorant composition were combined in an approximate ratio of 7:40:120 respectively, and mixed well in a bowl. The composition was applied to the strands of hair and left for about 15 to 25 minutes, The hair was rinsed well with water to remove the colorant. The hair was then shampooed and conditioned. The hair to which the composition was applied was both colored and highlighted, exhibiting variations in tonality and hue.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A one step method for simultaneously coloring and highlighting hair to provide hair fibers having variations in tonality and hue comprising the steps of:
   (a) combining (i) a powder composition comprised of at least one alkali metal or alkaline earth metal persulfate, (ii) an aqueous developer composition comprised of hydrogen peroxide; and (iii) an aqueous based colorant composition comprised of at least one primary intermediate and, optionally, at least one coupler for the formation of oxidation dyes; and
   (b) applying the mixture of (a) to the hair for a period of time sufficient to cause coloration and highlighting of the hair.

2. The method of claim 1 wherein the powder composition comprises 15–65% by weight of the total composition of sodium or potassium persulfate, or mixtures thereof.

3. The method of claim 2 wherein the powder composition further comprises 5–60% by weight of the total composition of one or more particulate fillers.

4. The method of claim 3 wherein the powder composition further comprises 0.01–2% by weight of inorganic colorant.

5. The method of claim 1 wherein the aqueous developer composition comprises, by weight of the total composition, 50–99% water, 1–30% hydrogen peroxide, and 0.01–30% of an oily phase.

6. The method of claim 5 wherein the aqueous developer composition additionally comprises 0.01–10% of a film forming polymer.

7. The method of claim 1 wherein the aqueous based colorant composition comprises, by weight of the total composition, 0.01–10% (combined weight) of at least one primary intermediate and at least one coupler for the formation of oxidation dyes.

8. The method of claim 7 wherein the aqueous based colorant has a pH of 7 to 11.

9. The method of claim 8 wherein the aqueous based colorant composition further comprises 0.01–20% of a cationic surfactant.

10. The method of claim 9 wherein the aqueous based colorant further comprises, by weight of the total composition, 0.1–20% humectant.

11. The method of claim 1 wherein the aqueous based colorant composition further comprises 0.1–10% of one or more protein derivatives.

12. The method of claim 1 wherein the mixture of (a) comprises, by weight of the total mixture, about 1–20% of (i), about 50–90% (ii), and about 10–60% (iii).

13. The method of claim 12 wherein the mixture of (a) has a pH of about 7.5 to 11.

14. The method of claim 13 wherein the mixture of (a) is applied to the hair for about 5 to 40 minutes and then rinsed out with water.

15. The method of claim 10 wherein the aqueous based colorant comprises 0.01–15% nonionic surfactant.

16. The method of claim 9 wherein the cationic surfactant is one or more cationic polymers.

* * * * *